(12) United States Patent
Madabhushi et al.

(10) Patent No.: US 12,014,488 B2
(45) Date of Patent: Jun. 18, 2024

(54) DISTINGUISHING COLON CANCER STAGES BASED ON COMPUTATIONALLY DERIVED MORPHOLOGICAL FEATURES OF CANCER NUCLEI

(71) Applicants: Case Western Reserve University, Cleveland, OH (US); The United States Government as Represented by the Department of Veteran Affairs, Washington, DC (US); UH Cleveland Medical Center, Cleveland, OH (US)

(72) Inventors: Anant Madabhushi, Shaker Heights, OH (US); Neeraj Kumar, Cleveland Heights, OH (US); Joseph E. Willis, Shaker Heights, OH (US)

(73) Assignees: Case Western Reserve University, Cleveland, OH (US); UH Cleveland Medical Center, Cleveland, OH (US); The United States Government as Represente, Washington, DC (US)

( * ) Notice: Subject to any disclaimer, the term of this patent is extended or adjusted under 35 U.S.C. 154(b) by 248 days.

(21) Appl. No.: 17/140,586

(22) Filed: Jan. 4, 2021

(65) Prior Publication Data

US 2021/0279864 A1  Sep. 9, 2021

Related U.S. Application Data

(60) Provisional application No. 62/984,813, filed on Mar. 4, 2020.

(51) Int. Cl.
*G06T 7/00* (2017.01)
*G06T 7/11* (2017.01)
(Continued)

(52) U.S. Cl.
CPC ............. *G06T 7/0012* (2013.01); *G06T 7/11* (2017.01); *G06T 7/41* (2017.01); *G06T 7/62* (2017.01);
(Continued)

(58) Field of Classification Search
CPC .......... G06T 7/0012; G06T 7/10; G06T 7/60; G06T 2207/30024; G06T 2207/30096;
(Continued)

(56) References Cited

U.S. PATENT DOCUMENTS 10,055,551 B2 *  8/2018  Agaian ................ G06T 7/0012
10,192,099 B2 *  1/2019  Agaian ................ G06V 20/69
(Continued)

FOREIGN PATENT DOCUMENTS

WO  WO-2018115055 A1 *  6/2018  ........... G06K 9/0014
WO  WO-2019105976 A1 *  6/2019  ......... G01N 15/1475

OTHER PUBLICATIONS

Wang, E.K.; Zhang, X.; Pan, L.; Cheng, C.; Dimitrakopoulou-Strauss, A.; Li, Y.; Zhe, N. Multi-Path Dilated Residual Network for Nuclei Segmentation and Detection. Cells 2019, 8, 499. https://doi.org/10.3390/cells8050499 (Year: 2019).*
(Continued)

*Primary Examiner* — John Villecco
*Assistant Examiner* — Courtney Joan Nelson
(74) *Attorney, Agent, or Firm* — Eschweiler & Potashnik, LLC

(57) ABSTRACT

Embodiments discussed herein facilitate determination of cancer stages based at least in part on shape, size, and/or texture features of cancer nuclei. One example embodiment is a method, comprising: accessing at least a portion of a digital whole slide image (WSI) comprising a tumor; segmenting (e.g., via a first deep learning model) the tumor on the at least the portion of the digital WSI; segmenting (e.g.,
(Continued)

via a second deep learning model) cancer nuclei in the segmented tumor; extracting one or more features from the segmented cancer nuclei; providing the one or more features extracted from the segmented cancer nuclei to a trained machine learning model; and receiving, from the machine learning model, an indication of a cancer stage of the tumor.

28 Claims, 4 Drawing Sheets

(51) Int. Cl.
G06T 7/41 (2017.01)
G06T 7/62 (2017.01)
G16H 10/40 (2018.01)
G16H 30/40 (2018.01)
G16H 50/20 (2018.01)
G16H 70/60 (2018.01)

(52) U.S. Cl.
CPC ............ *G16H 10/40* (2018.01); *G16H 30/40* (2018.01); *G16H 50/20* (2018.01); *G16H 70/60* (2018.01); *G06T 2207/20081* (2013.01); *G06T 2207/20084* (2013.01); *G06T 2207/30024* (2013.01); *G06T 2207/30028* (2013.01); *G06T 2207/30081* (2013.01); *G06T 2207/30096* (2013.01)

(58) Field of Classification Search
CPC . G06T 2207/10056; G06T 2207/20084; G06T 2207/30004; G06T 7/62; G06T 7/11; G06T 7/41; G06T 2207/20081; G06T 2207/30028; G06T 2207/30081; G16H 50/20; G16H 50/30; G16H 10/40; G16H 70/60; G16H 30/40; G06V 20/695; G06V 20/69
See application file for complete search history.

(56) References Cited

U.S. PATENT DOCUMENTS

| | | | |
|---|---|---|---|
| 2010/0098306 A1* | 4/2010 | Madabhushi | G06V 20/695 382/128 |
| 2015/0003716 A1* | 1/2015 | Lloyd | G06V 20/698 382/133 |
| 2017/0053398 A1* | 2/2017 | Mahoor | G06T 7/42 |
| 2017/0176565 A1* | 6/2017 | Kwak | A61B 5/4381 |
| 2018/0232883 A1* | 8/2018 | Sethi | G16H 30/40 |
| 2019/0042826 A1* | 2/2019 | Chang | G06T 7/11 |
| 2019/0156159 A1* | 5/2019 | Kopparapu | G06F 18/24147 |

OTHER PUBLICATIONS

J. T. Kwak and S. M. Hewitt, "Nuclear Architecture Analysis of Prostate Cancer via Convolutional Neural Networks," in IEEE Access, vol. 5, pp. 18526-18533, 2017, doi: 10.1109/ACCESS.2017.2747838 (Year: 2017).*

K. Kancherla and S. Mukkamala, "Early lung cancer detection using nucleus segementation based features," 2013 IEEE Symposium on Computational Intelligence in Bioinformatics and Computational Biology (CIBCB), Singapore, 2013, pp. 91-95, doi: 10.1109/CIBCB.2013.6595393 (Year: 2013).*

B. Akbar, V. P. Gopi and V. S. Babu, "Colon cancer detection based on structural and statistical pattern recognition," 2015 2nd International Conference on Electronics and Communication Systems (ICECS), Coimbatore, India, 2015, pp. 1735-1739, doi: 10.1109/ECS.2015.7124883 . . . (Year: 2015).*

M. A. Iftikhar, M. Hassan and H. Alquhayz, "A colon cancer grade prediction model using texture and statistical features, SMOTE and mRMR," 2016 19th International Multi-Topic Conference (INMIC), Islamabad, Pakistan, 2016, pp. 1-7, doi: 10.1109/INMIC.2016.7840161. (Year: 2016).*

S. Naik, S. Doyle, S. Agner, A. Madabhushi, M. Feldman and J. Tomaszewski, "Automated gland and nuclei segmentation for grading of prostate and breast cancer histopathology, " 2008 5th IEEE International Symposium on Biomedical Imaging: From Nano to Macro, Paris, France, 2008, pp. 284-287, (Year: 2008) doi: 10.1109/ISBI.2008.4540988. (Year: 2008).*

Jevtić P, Edens LJ, Vuković LD, Levy DL. Sizing and shaping the nucleus: mechanisms and significance. Curr Opin Cell Biol. Jun. 2014;28:16-27. doi: 10.1016/j.ceb.2014.01.003. Epub Feb. 4, 2014. PMID: 24503411; PMCID: PMC4061251. (Year: 2014).*

* cited by examiner

| Feature | Stage 2 vs. Stage 4 classification AUC±STD | P-value |
|---|---|---|
| Standard deviation of nuclei area | 0.74±0.10 | <0.001 |
| Average nuclei area | 0.63±0.13 | 0.015 |
| Average major length axis | 0.63±0.11 | 0.001 |
| Average nuclei perimeter | 0.67±0.10 | <0.001 |
| Kurtosis of nuclei area | 0.60±0.10 | 0.012 |
| All features combined | 0.78±0.09 | - |

FIG. 3

DISTINGUISHING COLON CANCER STAGES BASED ON COMPUTATIONALLY DERIVED MORPHOLOGICAL FEATURES OF CANCER NUCLEI

CROSS REFERENCE TO RELATED APPLICATIONS

This application claims the benefit of U.S. Provisional Patent Application No. 62/984,813 filed Mar. 4, 2020, entitled "COMPUTATIONALLY DERIVED MORPHOLOGICAL FEATURES OF CANCER NUCLEI FROM COLON WHOLE SLIDE IMAGES CAN DISTINGUISH STAGE 2 FROM STAGE 4 COLON CANCERS", the contents of which are herein incorporated by reference in their entirety.

FEDERAL FUNDING NOTICE

This invention was made with government support under CA199374, CA202752, CA208236, CA216579, CA220581, CA239055, EB028736, and RR012463 awarded by the National Institutes of Health; W81XWH-16-1-0329, W81XWH-18-1-0440, W81XWH-19-1-0668, and W81XWH-15-1-0558 awarded by the Department of Defense; 1451075 awarded by the National Science Foundation; and IBX004121A awarded by the Veterans Administration. The government has certain rights in the invention.

BACKGROUND

Machine learning analysis of digital whole slide images (WSI) has immense promise to affect how anatomic pathology is practiced. Computerized processing of these gigapixel images has the potential to facilitate a variety of clinical scenarios, including standardization of tumor morphological classifications, identification of unique intratumor regions of potential biological significance, and identification of important sub-visual features not currently appreciated by standard light microscopy techniques.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 3 illustrates a table showing the features identified based on the training set in the example use case as useful in discerning stage 2 and stage 4 colon cancer, in connection with various aspects discussed herein.

DETAILED DESCRIPTION

Various embodiments discussed herein include apparatus, systems, operations, methods, or other embodiments that facilitate use of computational image analysis to evaluate the role of size, shape, and texture features of cancer nuclei (e.g., nuclei of colon cancer) from whole slide images (WSIs) and/or portions thereof to distinguish between different cancer stages (e.g., Stage 2 and Stage 4 cancers, etc.).

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Embodiments include apparatus, systems, operations, methods, or other embodiments that can construct or employ a machine learning model to distinguish between cancer (e.g., colon cancer, etc.) stages (e.g., stage 2 and stage 4, etc.) based at least in part on size, shape, and/or texture features of cancer nuclei.

Figure 1:
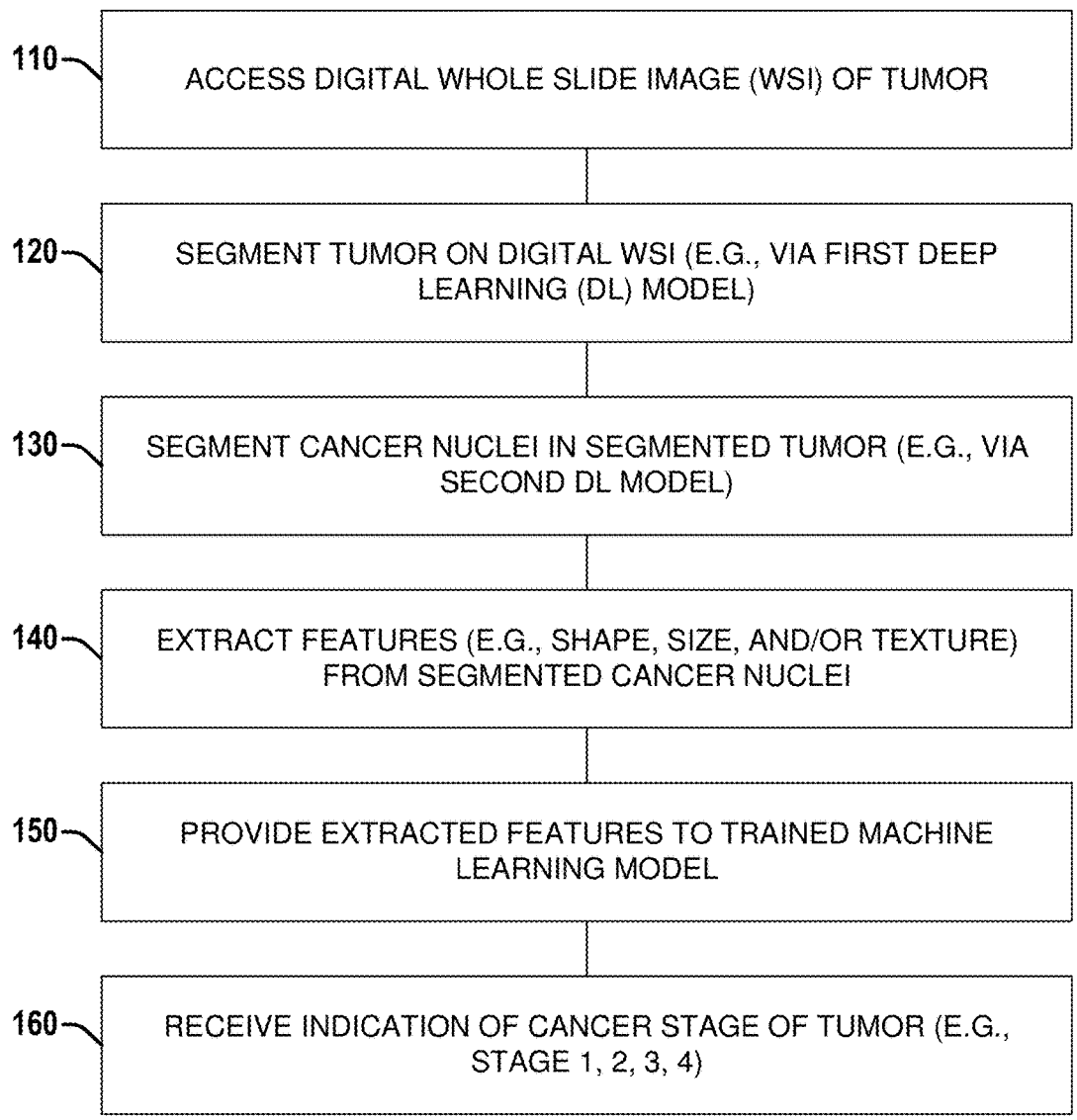
FIG. 1 illustrates a flow diagram of an example method/set of operations that can be performed by one or more processors to employ a machine learning model to distinguish between cancer stages based at least in part on size, shape, and/or texture features of cancer nuclei, in connection with various aspects discussed herein.

Referring to FIG. 1, illustrated is a flow diagram of an example method/set of operations 100 that can be performed by one or more processors to employ a machine learning model to distinguish between cancer stages based at least in part on size, shape, and/or texture features of cancer nuclei, in connection with various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, accessing at least a portion of a digital whole slide image (WSI) comprising a tumor. In various embodiments and in the example use case discussed below, the digital whole slide image (WSI) can be obtained via a system and/or apparatus implementing the set of operations 100, or can be obtained from a separate medical imaging system (e.g., optical microscope, etc.). Additionally, the digital WSI can be accessed contemporaneously with or at any point prior to performing the set of operations 100.

The set of operations 100 can further comprise, at 120, segmenting the tumor on the at least the portion of the digital WSI.

The set of operations 100 can further comprise, at 130, segmenting cancer nuclei in the segmented tumor.

The set of operations 100 can further comprise, at 140, extracting one or more features from the segmented cancer nuclei.

The set of operations 100 can further comprise, at 150, providing the one or more features extracted from the segmented cancer nuclei to a trained machine learning model.

The set of operations 100 can further comprise, at 160, receiving, from the machine learning model, an indication of a cancer stage of the tumor.

Additionally, or alternatively, set of operations 100 can comprise one or more other actions discussed herein in connection with determining a cancer stage based at least in part on size, shape, and/or texture features.

Figure 2:
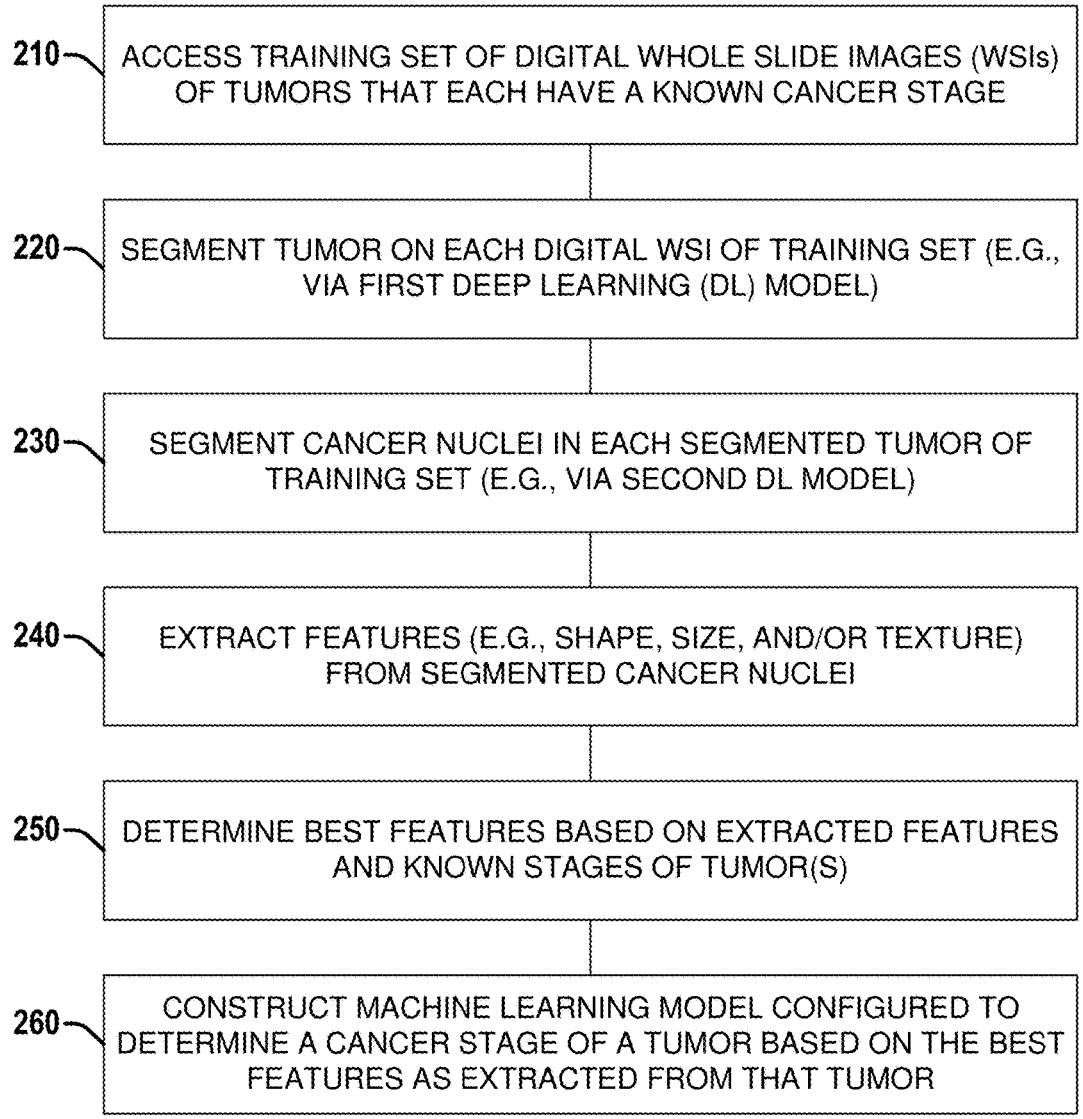
FIG. 2 illustrates a flow diagram of an example method/set of operations that can be performed by one or more processors to construct a machine learning model that can distinguish between cancer stages based at least in part on size, shape, and/or texture features of cancer nuclei, in connection with various aspects discussed herein.

Referring to FIG. 2, illustrated is a flow diagram of an example method/set of operations 200 that can be performed by one or more processors to construct a machine learning model that can distinguish between cancer stages based at least in part on size, shape, and/or texture features of cancer nuclei, in connection with various aspects discussed herein.

The set of operations 200 can comprise, at 210, accessing a training set comprising a plurality of digital whole slide images (WSIs), wherein each digital WSI of the plurality of digital WSIs comprises an associated tumor and a known associated cancer stage. In various embodiments, the digital WSI(s) can be obtained via a system and/or apparatus implementing the set of operations 200, or can be obtained from a separate medical imaging system (e.g., optical microscopy system). Additionally, the digital WSI(s) can be accessed contemporaneously with or at any point prior to performing the set of operations 200.

The set of operations 200 can further comprise, at 220, for each digital WSI of the training set, segmenting the associated tumor on that digital WSI.

The set of operations 200 can further comprise, at 230, for each digital WSI of the training set, segmenting associated cancer nuclei in the associated segmented tumor of that digital WSI.

The set of operations 200 can further comprise, at 240, for each digital WSI of the training set, extracting an associated value for each of a plurality of features from the associated segmented cancer nuclei of that digital WSI.

The set of operations 200 can further comprise, at 250, determining a set of best features from the plurality of features, based at least in part on the known associated cancer stage for each digital WSI of the training set and on the associated values for each of the plurality of features for each digital WSI of the training set; and The set of operations 200 can further comprise, at 260, constructing a machine learning model configured to determine an additional cancer stage for an additional digital WSI based at least in part on the set of best features.

Additionally, or alternatively, set of operations 200 can comprise one or more other actions discussed herein in connection with constructing a machine learning model that can distinguish between cancer stages based at least in part on size, shape, and/or texture features of cancer nuclei.

Additional aspects and embodiments are discussed below in connection with the following example use cases.

Example Use Case: Computationally Derived Morphological Features of Cancer Nuclei from Colon Whole Slide Images can Distinguish Stacie 2 from Stage 4 Colon Cancers The following discussion provides example embodiments in connection with an example use case involving constructing and employing a machine learning model that can distinguish between colon cancer stages 2 and 4 based at least in part on shape and/or texture features of colon cancer nuclei.

Introduction: Machine learning analysis of digital whole slide images (WSI) has immense promise to affect how anatomic pathology is practiced. Computerized processing of these gigapixel images has the potential to facilitate a variety of clinical scenarios—including standardization of tumor morphological classifications, identification of unique intra-tumor regions of potential biological significance; and identification of important sub-visual features not currently appreciated by standard light microscopy techniques. The example use case employed computational image analysis to evaluate the role of shape and texture features of nuclei of colon cancer from WSIs to distinguish between Stage 2 from Stage 4 cancers.

Design: One representative H&E stained digital WSI was obtained from 20 Stage 2 and 33 Stage 4 colon cancers. A fully-convolutional deep neural network with VGG-18 (named after the University of Oxford's Visual Geometry Group) architecture was trained to first identify the cancer extent on the WSIs. Another deep learning (DL) model based on Mask-RCNN (regional convolutional neural network) with Resnet-50 architecture was used to segment out all nuclei from within the identified cancer region. These two DL models were validated on publicly available datasets. Subsequently, a total of 146 shape, size and texture features were extracted from the tumor nuclei and Wilcoxon rank-sum test was used to select the most discriminatory features between Stage 2 and Stage 4 tumors. The selected features were then employed in a Random Forest (RF) classifier to distinguish Stage 2 and Stage 4 colon tumors.

Results: Only five out of the 146 nuclear features were found to be useful for discerning between Stage 2 and Stage 4 colon cancers. The classifier trained in a cross-validation setting using these five features yielded an average AUC of 0.78±0.09. The five discriminative features related to first order statistics of nuclear area, perimeter and length. Referring to FIG. 3, illustrated is a table showing the features identified based on the training set in the example use case as useful in discerning stage 2 and stage 4 colon cancer, in connection with various aspects discussed herein.

Conclusion: The results of the example use case suggest that nuclei of Stage 4 colon cancers tend to have a higher area, perimeter, and length, as well as more variance in nuclear area when compared with Stage 2 tumors.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to constructing and/or employing models that can distinguish between cancer stages based at least in part on nuclear size, shape, and/or texture features of cancer nuclei segmented via deep learned features or mappings that are not perceivable by the human eye, and involve computation that cannot be practically performed in the human mind. As one example, deep learning models as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 4:
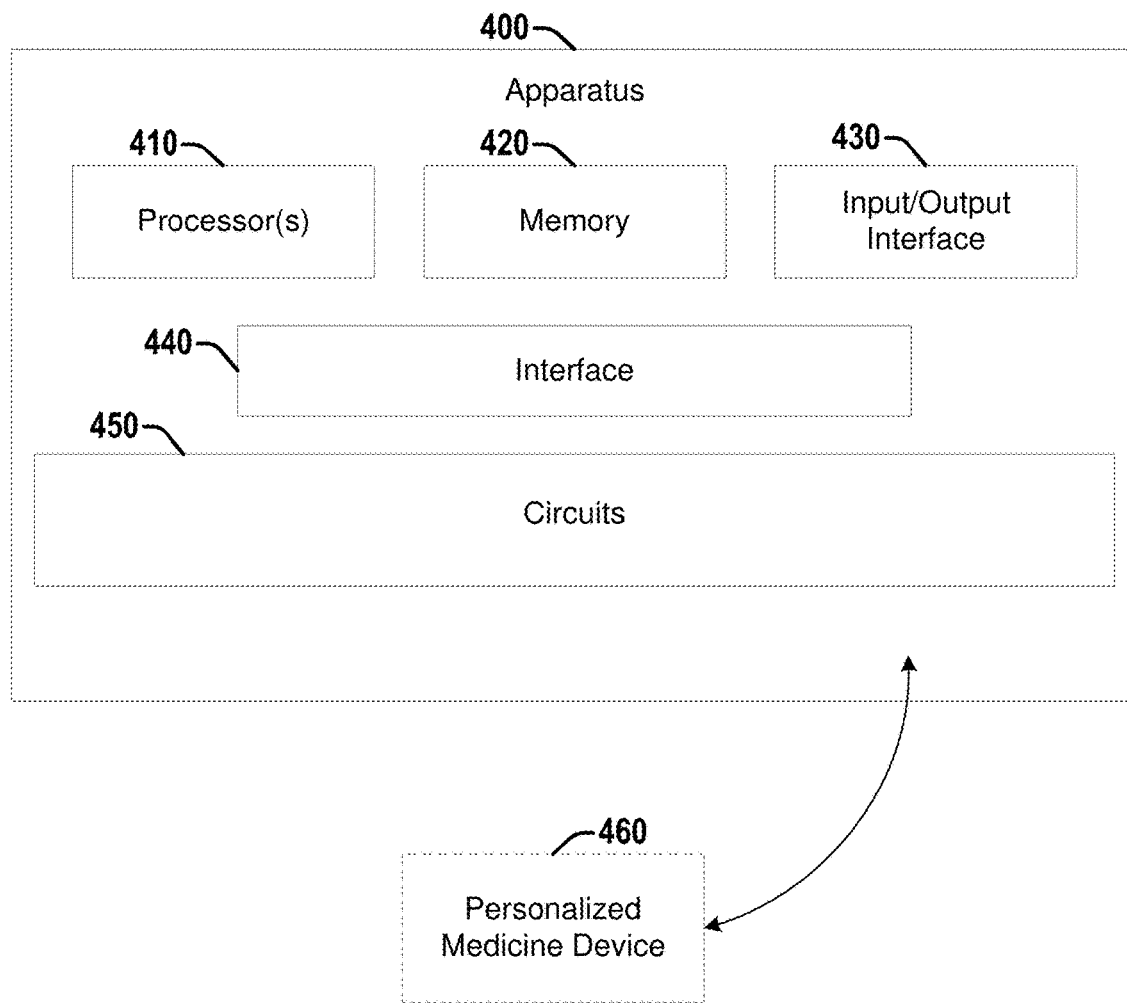
FIG. 4 illustrates a diagram of an example apparatus that can facilitate constructing and/or employing a machine learning model that can distinguish between cancer stages based at least in part on size, shape, and/or texture features of cancer nuclei, in connection with various aspects discussed herein.

Referring to FIG. 4, illustrated is a diagram of an example apparatus 400 that can facilitate constructing and/or employing a machine learning model that can distinguish between cancer stages based at least in part on size, shape, and/or texture features of cancer nuclei, in connection with various aspects discussed herein. Apparatus 400 can be configured to perform various techniques discussed herein, for example, various operations discussed in connection with sets of operations 100, 200, and/or other methods described herein. Apparatus 400 can comprise one or more processors 410 and memory 420. Processor(s) 410 can, in various embodiments, comprise circuitry such as, but not limited to, one or more single-core or multi-core processors. Processor(s) 410 can include any combination of general-purpose processors and dedicated processors (e.g., graphics processors, application processors, etc.). The processor(s) can be coupled with and/or can comprise memory (e.g., of memory 420) or storage and can be configured to execute instructions stored in the memory 420 or storage to enable various apparatus, applications, or operating systems to perform operations and/or methods discussed herein. Memory 420 can be configured to store one or more digital whole slide images (WSIs) (e.g., obtained via optical microscopes, etc.) of tumor(s). Each of the digital WSI(s) can comprise a plurality of pixels or voxels, each pixel or voxel having an associated intensity. Memory 420 can be further configured to store additional data involved in performing operations discussed herein, such as for constructing and/or employing a machine learning model that can distinguish between cancer stages based at least in part on size, shape, and/or texture features of cancer nuclei, in connection with various aspects discussed herein.

Apparatus 400 can also comprise an input/output (I/O) interface 430 (e.g., associated with one or more I/O devices), a set of circuits 450, and an interface 440 that connects the processor(s) 410, the memory 420, the I/O interface 430, and the set of circuits 450. I/O interface 430 can be configured to transfer data between memory 420, processor 410, circuits 450, and external devices, for example, medical imaging device(s) (e.g., optical microscopy system(s), etc.), and/or one or more remote devices for receiving inputs and/or providing outputs to a clinician, patient, etc., such as optional personalized medicine device 460.

The processor(s) 410 and/or one or more circuits of the set of circuits 450 can perform one or more acts associated with a method or set of operations discussed herein, such as set of operations 100, 200, etc. In various embodiments, different acts (e.g., different operations of a set of operations) can be performed by the same or different processor(s) 410 and/or one or more circuits of the set of circuits 450.

Apparatus 400 can optionally further comprise personalized medicine device 460. Apparatus 400 can be configured to provide the determination of cancer stage and/or other data to personalized medicine device 460. Personalized medicine device 460 may be, for example, a computer assisted diagnosis (CADx) system or other type of personalized medicine device that can be used to facilitate monitoring and/or treatment of an associated medical condition. In some embodiments, processor(s) 410 and/or one or more circuits of the set of circuits 450 can be further configured to control personalized medicine device 460 to display the segmented cancer on the WSI, the segmented cancer nuclei, values of one or more size/shape/texture feature(s), determination of cancer stage, and/or other data on a computer monitor, a smartphone display, a tablet display, or other displays.

Examples herein can include subject matter such as an apparatus, an optical microscopy system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for performing any operations and/or methods discussed herein, according to embodiments and examples described.

Nuclei of Stage 4 colon cancers tend to have a higher area, perimeter, and length as well as more variance in nuclear area compared to Stage 2 tumors, as determined by various embodiments described herein.

One embodiment includes a non-transitory computer-readable storage device storing computer-executable instructions that when executed control a processor to perform operations for distinguishing Stage 2 colon cancer tumors from Stage 4 colon cancer tumors, the operations comprising: accessing a digitized whole slide image (WSI) of a region of tissue demonstrating colon cancer; annotating a tumoral region represented in the digitized WSI using a first deep neural network configured to identify cancer extent on digitized WSI of tissue demonstrating colon cancer; generating a set of segmented cellular nuclei by segmenting cellular nuclei located within the tumoral region represented in the digitized WSI using a second, different deep learning model; extracting a set of discriminative features from the segmented cellular nuclei; computing, using a machine learning classifier configured to generate a probability that the tumoral region is Stage 2 or Stage 4 based on the set of discriminative features, a probability that the tumoral region is Stage 2 or Stage 4; and generating a classification of the tumoral region as Stage 2 or Stage 4 based, at least in part, on the probability.

Operations, methods, and other embodiments described herein include acquiring electronic data, reading from a computer file, receiving a computer file, reading from a computer memory, or other computerized activity not practically performed in a human mind, at least because a first deep neural network configured to identify cancer extent on digitized WSI of tissue demonstrating colon cancer cannot be practically performed or implemented in a human mind. Additionally, for example, computing, using a machine learning classifier configured to generate a probability that the tumoral region is Stage 2 or Stage 4 based on the set of discriminative features, a probability that the tumoral region is Stage 2 or Stage 4 may include acquiring electronic data, reading from a computer file, receiving a computer file, reading from a computer memory, or other computerized activity not practically performed in a human mind.

In one embodiment, the first deep neural network comprises a fully-convolutional deep neural network having a VGG-18 architecture. In another embodiment, the first deep neural network may comprise a fully-convolutional deep neural network having another, different architecture. In another embodiment, the operations may further comprise training the first deep neural network according to various techniques described herein.

In one embodiment, the second, different deep learning model comprises a deep learning model having a Mask-RCNN with Resnet-50 architecture. In another embodiment, the second, different deep learning model may comprise a deep learning model having another, different architecture. In another embodiment, the operations may further comprise training the second, different deep learning model according to various techniques described herein.

In one embodiment, the set of discriminative features comprises a standard deviation of nuclear area feature, an average nuclear area feature, an average major axis length feature, an average nuclei perimeter feature, and a kurtosis of nuclei area feature. In another embodiment, the set of discriminative features may comprise another, different number of discriminative features, or may comprise other, different discriminative features. In various embodiments described herein, the set of discriminative features comprises sub-visual features that are not practically discernible by the human mind or using pencil or paper.

In one embodiment, the machine learning classifier comprises a random forest classifier. In another embodiment, the machine learning classifier may comprise another, different machine learning classifier configured to generate a probability that the tumoral region is Stage 2 or Stage 4 based on the set of discriminative features.

In one embodiment, the operations further comprise displaying the classification. In another embodiment, the operations may further comprise displaying at least one of the probability, the set of discriminative features, the set of segmented nuclei, the tumoral region, or the digitized WSI.

Displaying the classification or at least one of the probability, the set of discriminative features, the set of segmented nuclei, the tumoral region, or the digitized WSI may comprise generating a visual output of the classification or at least one of the probability, the set of discriminative features, the set of segmented nuclei, the tumoral region, or the digitized WSI, and displaying the visual output on a computer monitor, a smartphone display, a tablet display, or other displays. Displaying the classification or at least one of the probability, the set of discriminative features, the set of segmented nuclei, the tumoral region, or the digitized WSI may also include printing the classification or at least one of the probability, the set of discriminative features, the set of segmented nuclei, the tumoral region, or the digitized WSI. Displaying the classification or at least one of the probability, the set of discriminative features, the set of segmented nuclei, the tumoral region, or the digitized WSI may also include controlling a colon cancer assessment system, a personalized medicine system, a monitor, or other display, to display operating parameters or characteristics of a deep learning model or a machine learning classifier, during both training and testing, or during clinical operation of the deep learning model or the machine learning classifier. By displaying the classification or at least one of the probability, the set of discriminative features, the set of segmented nuclei, the tumoral region, or the digitized WSI, or operating parameters or characteristics of the deep learning model or machine learning classifier, example embodiments provide a timely and intuitive way for a human practitioner to distinguish colon cancer as Stage 2 or Stag 4, thus improving on existing approaches to distinguishing colon cancer as Stage 2 or Stage 4.

One embodiment comprises an apparatus comprising: a memory; and a set of processors configured to: access a digitized whole slide image (WSI) of a region of tissue demonstrating colon cancer; annotate a tumoral region represented in the digitized WSI using a first deep neural network configured to identify cancer extent on digitized WSI of tissue demonstrating colon cancer; generate a set of segmented cellular nuclei by segmenting cellular nuclei located within the tumoral region represented in the digitized WSI using a second, different deep learning model; extract a set of discriminative features from the segmented cellular nuclei; compute, using a machine learning classifier configured to generate a probability that the tumoral region is Stage 2 or Stage 4 based on the set of discriminative features, a probability that the tumoral region is Stage 2 or Stage 4; and generate a classification of the tumoral region as Stage 2 or Stage 4 based, at least in part, on the probability.

Example 1 is a non-transitory computer-readable medium storing computer-executable instructions that, when executed, cause a processor to perform operations, comprising: accessing at least a portion of a digital whole slide image (WSI) comprising a tumor; segmenting the tumor on the at least the portion of the digital WSI; segmenting cancer nuclei in the segmented tumor; extracting one or more features from the segmented cancer nuclei; providing the one or more features extracted from the segmented cancer nuclei to a trained machine learning model; and receiving, from the machine learning model, an indication of a cancer stage of the tumor.

Example 2 comprises the subject matter of any variation(s) of any of example(s) 1, wherein the machine learning model is one of, or an ensemble of two or more of, a logistic regression model, a Cox regression model, a Least Absolute Shrinkage and Selection Operator (LASSO) regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, an elastic net, a Gaussian process classification, or a nearest neighbors classification.

Example 3 comprises the subject matter of any variation(s) of any of example(s) 1-2, wherein the one or more features comprise at least one of: a statistic of at least one shape feature of the segmented cancer nuclei, the statistic of at least one size feature of the segmented cancer nuclei, or the statistic of at least one texture feature of the segmented cancer nuclei.

Example 4 comprises the subject matter of any variation(s) of any of example(s) 3, wherein the statistic is one of a mean, a median, a standard deviation, a skewness, a kurtosis, a range, a minimum, a maximum, a percentile, or histogram frequencies.

Example 5 comprises the subject matter of any variation(s) of any of example(s) 3-4, wherein the at least one size feature of the segmented cancer nuclei comprises one or more of an area, a major axis length, or a perimeter.

Example 6 comprises the subject matter of any variation(s) of any of example(s) 1-5, wherein segmenting the tumor on the at least the portion of the digital WSI comprises segmenting the tumor on the at least the portion of the digital WSI via a first deep learning (DL) model.

Example 7 comprises the subject matter of any variation(s) of any of example(s) 6, wherein the first DL model is a fully convolutional deep neural network with a Visual Geometry Group (VGG)-18 architecture.

Example 8 comprises the subject matter of any variation(s) of any of example(s) 6-7, wherein the first DL model employs one of the following optimizers: an Adam optimizer, a stochastic gradient descent (SGD) optimizer, a SGD optimizer with momentum, or a SGD optimizer with Nesterov momentum.

Example 9 comprises the subject matter of any variation(s) of any of example(s) 1-8, wherein segmenting cancer nuclei in the segmented tumor comprises segmenting cancer nuclei in the segmented tumor via a second deep learning (DL) model.

Example 10 comprises the subject matter of any variation(s) of any of example(s) 9, wherein the first DL model is a Mask-RCNN (Regional Convolutional Neural Network) with a Residual Network (Resnet)-50 architecture.

Example 11 comprises the subject matter of any variation(s) of any of example(s) 9-10, wherein the second DL model employs one of the following optimizers: an Adam optimizer, a stochastic gradient descent (SGD) optimizer, a SGD optimizer with momentum, or a SGD optimizer with Nesterov momentum.

Example 12 comprises the subject matter of any variation(s) of any of example(s) 1-11, wherein the cancer is prostate cancer.

Example 13 comprises the subject matter of any variation(s) of any of example(s) 12, wherein the cancer stage is one of stage 2 or stage 4.

Example 14 is a non-transitory computer-readable medium storing computer-executable instructions that, when executed, cause a processor to perform operations, comprising: accessing a training set comprising a plurality of digital whole slide images (WSIs), wherein each digital WSI of the plurality of digital WSIs comprises an associated tumor and a known associated cancer stage; for each digital WSI of the training set: segmenting the associated tumor on that digital WSI; segmenting associated cancer nuclei in the associated segmented tumor of that digital WSI; and extracting an associated value for each of a plurality of features from the associated segmented cancer nuclei of that digital WSI; determining a set of best features from the plurality of features, based at least in part on the known associated cancer stage for each digital WSI of the training set and on the associated values for each of the plurality of features for each digital WSI of the training set; and constructing a machine learning model configured to determine an additional cancer stage for an additional digital WSI based at least in part on the set of best features.

Example 15 comprises the subject matter of any variation(s) of any of example(s) 14, wherein determining the set of best features comprises determining the set of best features via a Wilcoxon rank-sum test.

Example 16 comprises the subject matter of any variation(s) of any of example(s) 14-15, wherein the machine learning model is one of, or an ensemble of two or more of, a logistic regression model, a Cox regression model, a Least Absolute Shrinkage and Selection Operator (LASSO) regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, an elastic net, a Gaussian process classification, or a nearest neighbors classification.

Example 17 comprises the subject matter of any variation(s) of any of example(s) 14-16, wherein the one or more features comprise at least one of: a statistic of at least one shape feature of the segmented cancer nuclei, the statistic of at least one size feature of the segmented cancer nuclei, or the statistic of at least one texture feature of the segmented cancer nuclei.

Example 18 comprises the subject matter of any variation(s) of any of example(s) 17, wherein the statistic is one of a mean, a median, a standard deviation, a skewness, a kurtosis, a range, a minimum, a maximum, a percentile, or histogram frequencies.

Example 19 comprises the subject matter of any variation(s) of any of example(s) 17-18, wherein the at least one size feature of the segmented cancer nuclei comprises one or more of an area, a major axis length, or a perimeter.

Example 20 comprises the subject matter of any variation(s) of any of example(s) 14-19, wherein, for each digital WSI of the training set, segmenting the associated tumor on that digital WSI comprises segmenting the associated tumor on that digital WSI via a first deep learning (DL) model.

Example 21 comprises the subject matter of any variation(s) of any of example(s) 14-20, wherein, for each digital WSI of the training set, segmenting the associated cancer nuclei in the associated segmented tumor of that digital WSI comprises segmenting the associated cancer nuclei in the associated segmented tumor of that digital WSI via a second deep learning (DL) model.

Example 22 is an apparatus, comprising: memory configured to store at least a portion of a digital whole slide image (WSI) comprising a tumor; one or more processors configured to perform operations comprising: segmenting the tumor on the at least the portion of the digital WSI; segmenting cancer nuclei in the segmented tumor; extracting one or more features from the segmented cancer nuclei; providing the one or more features extracted from the segmented cancer nuclei to a trained machine learning model; and receiving, from the machine learning model, an indication of a cancer stage of the tumor.

Example 23 comprises the subject matter of any variation(s) of any of example(s) 22, wherein the machine learning model is one of, or an ensemble of two or more of, a logistic regression model, a Cox regression model, a Least Absolute Shrinkage and Selection Operator (LASSO) regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, an elastic net, a Gaussian process classification, or a nearest neighbors classification.

Example 24 comprises the subject matter of any variation(s) of any of example(s) 22-23, wherein the one or more features comprise at least one of: a statistic of at least one shape feature of the segmented cancer nuclei, the statistic of at least one size feature of the segmented cancer nuclei, or the statistic of at least one texture feature of the segmented cancer nuclei.

Example 25 comprises the subject matter of any variation(s) of any of example(s) 24, wherein the statistic is one of a mean, a median, a standard deviation, a skewness, a kurtosis, a range, a minimum, a maximum, a percentile, or histogram frequencies.

Example 26 comprises the subject matter of any variation(s) of any of example(s) 24-25, wherein the at least one size feature of the segmented cancer nuclei comprises one or more of an area, a major axis length, or a perimeter.

Example 27 comprises the subject matter of any variation(s) of any of example(s) 22-26, wherein segmenting the tumor on the at least the portion of the digital WSI comprises segmenting the tumor on the at least the portion of the digital WSI via a first deep learning (DL) model.

Example 28 comprises the subject matter of any variation(s) of any of example(s) 22-27, wherein segmenting cancer nuclei in the segmented tumor comprises segmenting cancer nuclei in the segmented tumor via a second deep learning (DL) model.

Example 29 comprises an apparatus comprising means for executing any of the described operations of examples 1-28.

Example 30 comprises a computer-readable medium that stores instructions for execution by a processor to perform any of the described operations of examples 1-28.

Example 31 comprises an apparatus comprising: a memory; and one or more processors configured to: perform any of the described operations of examples 1-28.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
    accessing a segmented cancer nuclei in a segmented tumor from at least a portion of a digital whole slide image (WSI) comprising a tumor identified as having cancer present;
    extracting a plurality of features from the segmented cancer nuclei, wherein the plurality of features comprise a standard deviation of nuclear area feature, an average nuclear area feature, an average major axis length feature, an average nuclei perimeter feature, and a kurtosis of nuclei area feature;
    providing the plurality of features extracted from the segmented cancer nuclei to a trained machine learning model; and
    receiving, from the trained machine learning model, an indication of a cancer stage of the tumor identified as having cancer present based upon the plurality of features extracted from the segmented cancer nuclei, wherein the indication of the cancer stage differentiates between different stages of cancer within the tumor identified as having cancer present.

2. The non-transitory computer-readable medium of claim 1, wherein the operations further comprise:
    generating a probability that the tumor is Stage 2 or Stage 4 based on the plurality of features; and
    generating a classification of the tumor as Stage 2 or Stage 4 based, at least in part, on the probability.

3. The non-transitory computer-readable medium of claim 1, wherein the plurality of features comprise at least one of: a statistic of at least one shape feature of the segmented cancer nuclei, the statistic of at least one size feature of the segmented cancer nuclei, or the statistic of at least one texture feature of the segmented cancer nuclei.

4. The non-transitory computer-readable medium of claim 3, wherein the statistic is one of a mean, a median, a standard deviation, a skewness, a kurtosis, a range, a minimum, a maximum, a percentile, or histogram frequencies.

5. The non-transitory computer-readable medium of claim 3, wherein the at least one size feature of the segmented cancer nuclei comprises one or more of an area, a major axis length, or a perimeter.

6. The non-transitory computer-readable medium of claim 1, wherein the indication of the cancer stage of the tumor is a probability that the tumor is within one of the different stages of cancer.

7. The non-transitory computer-readable medium of claim 6, wherein the operations further comprise:
    segmenting the tumor on the at least the portion of the digital WSI comprises segmenting the tumor on the at least the portion of the digital WSI via a first deep learning (DL) model, wherein the first DL model is a fully convolutional deep neural network with a Visual Geometry Group (VGG)-18 architecture.

8. The non-transitory computer-readable medium of claim 6, wherein the operations further comprise:
    segmenting the tumor on the at least the portion of the digital WSI comprises segmenting the tumor on the at least the portion of the digital WSI via a first deep learning (DL) model, wherein the first DL model employs one of the following optimizers: an Adam optimizer, a stochastic gradient descent (SGD) optimizer, a SGD optimizer with momentum, or a SGD optimizer with Nesterov momentum.

9. The non-transitory computer-readable medium of claim 1, wherein the operations further include:
    segmenting the WSI to identify cancer within the WSI using a first deep learning (DL) model; and
    segmenting the segmented cancer nuclei in the identified cancer using a second deep learning (DL) model that is different than the first DL model.

10. The non-transitory computer-readable medium of claim 9, wherein the first DL model is a VGG-18 and the second DL model is a Mask-RCNN (Regional Convolutional Neural Network) with a Residual Network (Resnet)-50 architecture.

11. The non-transitory computer-readable medium of claim 9, wherein the trained machine learning model distinguishes segmented cancer nuclei of a higher stage cancer as having a larger area, a larger perimeter, a larger length, and a greater variance in nuclear area than segmented cancer nuclei of a lower stage cancer, the higher stage cancer and the lower stage cancer being of the tumor identified as having cancer present.

12. The non-transitory computer-readable medium of claim 1, wherein the segmented cancer nuclei comprises prostate cancer.

13. The non-transitory computer-readable medium of claim 12, wherein the cancer stage is one of stage 2 or stage 4.

14. An apparatus, comprising:
    memory configured to store at least a portion of a digital whole slide image (WSI) comprising a tumor identified as having cancer present;
    one or more processors configured to perform operations comprising:
        segmenting the tumor on the at least the portion of the digital WSI;
        segmenting cancer nuclei in the segmented tumor;
        extracting one or more features from the segmented cancer nuclei;
        providing the one or more features extracted from the segmented cancer nuclei to a trained machine learning model;
        receiving, from the trained machine learning model, an indication of a cancer stage of the tumor identified as having cancer present based upon the one or more features extracted from the segmented cancer nuclei, wherein the indication of the cancer stage differentiates between different stages of cancer within the tumor identified as having cancer present and wherein the indication of the cancer stage of the tumor is a probability that the tumor is within one of the cancer stages; and
    wherein the trained machine learning model is configured to distinguish segmented cancer nuclei of a higher stage cancer as having a larger area, a larger perimeter, a larger length, and a greater variance in nuclear area than segmented cancer nuclei of a lower stage cancer, the higher stage cancer and the lower stage cancer being of the tumor identified as having cancer present.

15. The apparatus of claim 14, wherein the one or more features comprise a standard deviation of nuclear area feature, an average nuclear area feature, an average major axis length feature, an average nuclei perimeter feature, and a kurtosis of nuclei area feature.

16. The apparatus of claim 14, wherein the one or more features comprise at least one of: a statistic of at least one shape feature of the segmented cancer nuclei, the statistic of at least one size feature of the segmented cancer nuclei, or the statistic of at least one texture feature of the segmented cancer nuclei.

17. The apparatus of claim 16, wherein the statistic is one of a mean, a median, a standard deviation, a skewness, a kurtosis, a range, a minimum, a maximum, a percentile, or histogram frequencies.

18. The apparatus of claim 16, wherein the at least one size feature of the segmented cancer nuclei comprises one or more of an area, a major axis length, or a perimeter.

19. The apparatus of claim 14, wherein segmenting the tumor on the at least the portion of the digital WSI comprises segmenting the tumor on the at least the portion of the digital WSI via a first deep learning (DL) model.

20. The apparatus of claim 14, wherein segmenting cancer nuclei in the segmented tumor comprises segmenting cancer nuclei in the segmented tumor via a second deep learning (DL) model.

21. A method, comprising:
accessing a segmented cancer nuclei in a segmented colon cancer tumor from at least a portion of a digitized image having a tumor identified as having cancer present;
extracting one or more features from the segmented cancer nuclei;
providing the one or more extracted features extracted from the segmented cancer nuclei to a trained machine learning model; and
receiving, from the trained machine learning model, an indication of a cancer stage of the tumor identified as having cancer present based upon the one or more extracted features, wherein the indication of the cancer stage differentiates between different stages of cancer within the tumor identified as having cancer present; and
wherein the trained machine learning model is configured to distinguish segmented cancer nuclei of a higher stage cancer as having a larger area, a larger perimeter, a larger length, and a greater variance in nuclear area than segmented cancer nuclei of a lower stage cancer, the higher stage cancer and the lower stage cancer being of the tumor identified as having cancer present.

22. The method of claim 21, wherein the one or more features comprise a standard deviation of nuclear area feature, an average nuclear area feature, an average major axis length feature, an average nuclei perimeter feature, and a kurtosis of nuclei area feature.

23. The method of claim 21, wherein the trained machine learning model is configured to distinguish stage 2 colon cancer from stage 4 colon cancer.

24. The method of claim 21, wherein the one or more features comprise at least one of: a statistic of at least one shape feature of the segmented cancer nuclei, the statistic of at least one size feature of the segmented cancer nuclei, or the statistic of at least one texture feature of the segmented cancer nuclei.

25. The method of claim 24, wherein the indication of the cancer stage of the tumor is a probability that the tumor is within one of the different stages of cancer.

26. The method of claim 24, wherein the at least one size feature of the segmented cancer nuclei comprises one or more of an area, a major axis length, or a perimeter.

27. The method of claim 21, further comprising:
segmenting the digitized image to identify cancer within the digitized image using a first deep learning model; and
segmenting the segmented cancer nuclei in the identified cancer using a second deep learning model that is different than the first deep learning model.

28. The method of claim 27, wherein the first deep learning model is a VGG-18 and the second deep learning model is a Mask-RCNN (Regional Convolutional Neural Network) with a Residual Network (Resnet)-50 architecture.

* * * * *